(12) United States Patent
Frezza

(10) Patent No.: US 7,938,816 B2
(45) Date of Patent: May 10, 2011

(54) INFUSION BAG WITH INTEGRATED RINSING SYSTEM

(75) Inventor: Pierre Frezza, Charly (FR)

(73) Assignee: Laboratoire Aguettant, Lyons (FR)

( * ) Notice: Subject to any disclaimer, the term of this patent is extended or adjusted under 35 U.S.C. 154(b) by 0 days.

(21) Appl. No.: 12/756,837

(22) Filed: Apr. 8, 2010

(65) Prior Publication Data

US 2010/0228189 A1 Sep. 9, 2010

Related U.S. Application Data

(63) Continuation of application No. 11/597,381, filed as application No. PCT/FR2005/050414 on Jun. 2, 2005, now Pat. No. 7,722,594.

(30) Foreign Application Priority Data

Jun. 2, 2004 (FR) .................................. 04 05919

(51) Int. Cl.
*A61B 19/00* (2006.01)
(52) U.S. Cl. ............... 604/410; 604/80; 604/82; 604/87; 604/92; 604/408; 604/409; 604/416; 604/257; 604/173; 604/262; 604/5.01; 604/210; 206/219; 206/221; 206/222; 206/469; 383/210
(58) Field of Classification Search ............... 604/80, 604/82, 87, 92, 408–410, 416, 5.01, 210, 604/257, 173, 262; 206/219, 221, 222, 469; 308/210, 211; 383/38
See application file for complete search history.

(56) References Cited

U.S. PATENT DOCUMENTS

| | | | |
|---|---|---|---|
| 2,887,109 A | 5/1959 | Barrington | |
| 3,217,711 A | 11/1965 | Dayton et al. | |
| 4,248,226 A | 2/1981 | Pitchford | |
| 4,324,238 A | 4/1982 | Genese et al. | |
| 4,331,264 A | 5/1982 | Staar | |
| 4,396,383 A | 8/1983 | Hart | |
| 4,770,295 A | 9/1988 | Carveth et al. | |
| 4,810,451 A | 3/1989 | Ermert et al. | |
| 4,994,056 A | 2/1991 | Ikeda | |
| 4,997,083 A | 3/1991 | Loretti et al. | |
| 5,076,933 A | 12/1991 | Glenn et al. | |
| 5,536,469 A | 7/1996 | Jonsson et al. | |
| 5,560,403 A | 10/1996 | Balteau et al. | |
| 5,605,540 A | 2/1997 | Utterberg | |
| 5,643,205 A | 7/1997 | Utterberg | |
| 6,641,307 B2 | 11/2003 | Matsuda et al. | |
| 7,055,683 B2 | 6/2006 | Bourque et al. | |
| 2004/0004010 A1 | 1/2004 | Versluys | |

FOREIGN PATENT DOCUMENTS

EP 1 060 754 A1 12/2000
WO WO 88/19188 12/1988

*Primary Examiner* — Nicholas D Lucchesi
*Assistant Examiner* — Scott Medway
(74) *Attorney, Agent, or Firm* — Oliff & Berridge, PLC

(57) ABSTRACT

The invention relates to a medical bag which is intended for the infusion of a medicament by means of gravity. The inventive bag comprises: at least two compartments, namely a first compartment (1) containing a medicament in the form of a solution and a second compartment (2) containing a rinsing solution; and means for separating/communicating the compartments, which prevent the rinsing solution from automatically entering the medicament compartment except at the end of the infusion period. The rinsing solution ends the infusion, by rinsing the medicament bag and the infusion line, such as to prevent any risk of contamination or leakage of residual medicament from the bag or line.

8 Claims, 5 Drawing Sheets

INFUSION BAG WITH INTEGRATED RINSING SYSTEM

This is a Continuation of application Ser. No. 11/597,381, filed Feb. 15, 2007, which in turn is a U.S. National Stage Application of PCT/FR2005/050414, filed Jun. 2, 2005, which claims priority to French Application No. FR 04.05919, filed Jun. 2, 2004. The disclosures of each of these applications is hereby incorporated by reference herein in its entirety.

BACKGROUND OF THE INVENTION

The present invention relates to the infusion of medication contained in a flexible bag, which flows into the veins of a patient via an infusion line, under the effect of gravity, the bag being suspended above the patient.

More particularly, the invention relates to a bag for medical use for infusing medication by gravity, comprising at least two compartments, one containing medication and the other containing a rinsing solution, and separation/communication means for automatically rinsing the medication bag and infusion line.

The invention is intended to solve, simply and inexpensively, two major problems encountered with this type of infusion, namely:
- the loss of some of the medication: The infusion line has a non-negligible volume, in particular in the case of small infusion bags. The amount of medication remaining in the line plus the residual amount contained in the bag is not infused into the patient who thus does not receive the prescribed dose;
- the risk of contamination due to the toxicity of the medication: the medication infused may be extremely toxic or allergenic (cancer medication, antibiotics, etc.) and there may be a risk of contamination when the care personnel purges the air from the perfusion line before connecting up to the patient or when disconnecting the infusion line.

The solution to these two problems consists in rinsing the line before and after infusion and rinsing the bag after infusion using a harmless, inexpensive solution (isotonic sodium chloride for example).

DESCRIPTION OF THE PRIOR ART

Devices are already known which can at least partially rinse the bag/line, limiting medication loss and the risks for care personnel.

U.S. Pat. No. 5,242,392 describes an infusion system comprising a chamber for a rinsing liquid connected to the infusion tubing between the medication bag and the injection device and located lower than the medication bag. When the medication has been administered, the rinsing solution rinses the infusion tubing and injection device automatically.

Patent FR 2 794 983 describes a closed-circuit infusion system comprising at least one medication bag and dispensing and infusion means, associated with a rinsing bag in such a way that the rinsing solution can flow through the dispensing and infusion means, and also selection means allowing the medication and/or the rinsing solution to flow through the dispensing and infusion means.

Patent FR 2 306 711 describes an infusion device comprising at least two infusion containers suspended at different heights, whose tubes are connected for example using a Y-shaped connection piece, and a valve device with two inlets whose operation is linked to the difference in height between the infusion containers which causes a difference in height between the columns of liquid.

Documents WO 92/11881, U.S. Pat. No. 4,512,764, WO 95/09020, EP 0 790 064, U.S. Pat. No. 4,623,334 and WO 03/077974 describe infusion or injection systems comprising devices for rinsing the infusion line or injection system.

These devices do not provide a satisfactory solution to the problems of safety and effectiveness of the infusion systems:
- If the bag contains air, it may be completely emptied but a relatively large part of the infusion line will contain air and the line cannot be rinsed since the air contained in the line would be injected in the patient (risk of air embolism). The presence of the nurse is therefore required before the end of infusion in order to carry out rinsing at the exact moment when the bag is completely emptied, before some of the line fills with air.
- If the bag does not contain air, it cannot be completely emptied and the residual liquid contained in the bag will not be injected into the patient. In this case, the line may be rinsed, but not the bag.
- In all cases, the intervention of the nurse is required, entailing extra work.

SUMMARY OF THE INVENTION

The present invention is intended to improve the safety and effectiveness of infusion systems by virtue of a device for automatically rinsing the line and the bag after infusion, without the nurse's intervention.

The present invention relates to a bag for medical use for infusing medication by gravity, comprising at least two compartments, one containing medication in the form of a solution and the other(s) containing a rinsing solution, and compartment separation/communication means which allow the rinsing solution to enter the compartment containing the medication automatically only after infusion. The rinsing solution completes the infusion, rinsing the medication bag and the infusion line, thus eliminating the risk of contamination and the loss of residual medication in the bag and that contained in the infusion line.

The basic principle of the invention consists in using the vacuum created in the medication bag at the end of infusion owing to the water column height in the infusion line. This vacuum gradually increases at the end of infusion, as the bag becomes flattened through a "siphon" effect. This vacuum can reach around −100 mb.

The rinsing liquid, which is at atmospheric pressure, is drawn into the compartment containing the medication, which in turn is at a vacuum pressure with respect to atmospheric pressure.

The separation/communication means comprise a breakable device between the compartment containing the medication and the compartment (one of the compartments) containing the solution and a device for ensuring automatic communication between the compartment containing the medication and the compartment containing the solution or between the two compartments containing the solution.

The device for ensuring automatic communication between the compartments may be a communication channel positioned above the level of the liquid in said compartments when the bag is suspended vertically.

As a variant, the device for ensuring automatic communication between the compartments may be a pressure-threshold valve.

The compartment or compartments containing the rinsing solution may comprise a narrow area towards the top of the bag.

DESCRIPTION OF THE DRAWINGS

The attached drawings illustrate the present invention in more detail.

DESCRIPTION OF THE PREFERRED EMBODIMENTS

Figure 1:
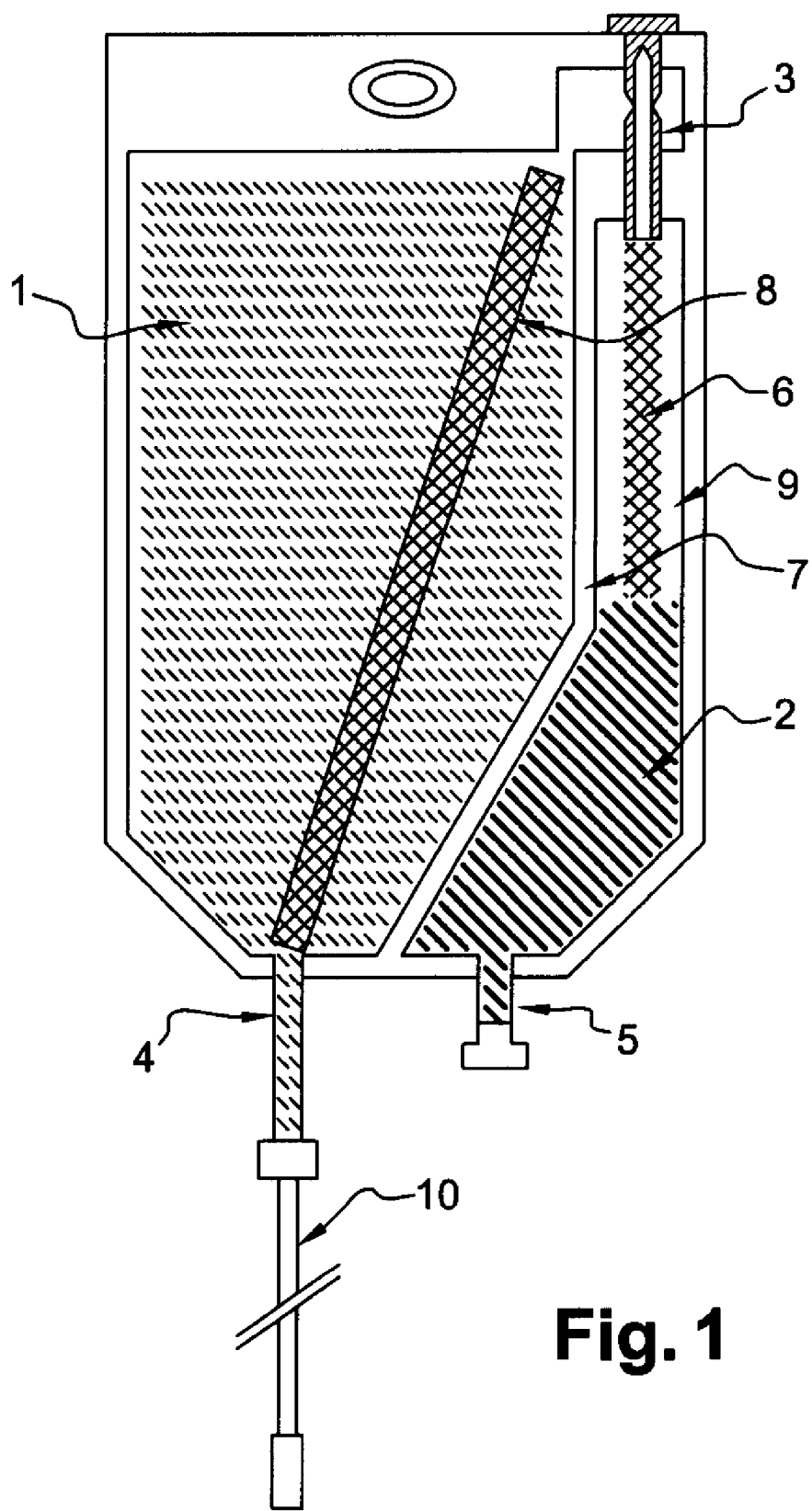
FIG. 1 shows an infusion bag with two compartments comprising a communication channel.

According to a first embodiment of the invention shown in FIG. 1, use is made of a flexible infusion bag separated into two juxtaposed compartments (1) and (2), one (1) of which contains the medication and the other (2) the rinsing solution. Compartment (1) comprises an access (4) for filling the bag and connecting to the infusion line (10). Compartment (2) comprises a narrow area (9) at the top of the bag and an access (5) for filling said compartment. The two compartments are separated by a substantially vertical wall (7) whose upper part comprises a breakable device (3) designed to ensure the seal between the two compartments when it is intact and to allow communication between the two compartments when it is broken by the nurse by mechanical intervention on the outside of the bag. This device is imperatively placed above the level of the liquids when the bag is suspended.

Compartments (1) and (2) are filled without the addition of air. Said compartments comprise means (8) and (6) for preventing the flow path of the liquid from being sealed up completely when the bag flattens. These means (8) and (6) may consist for example of a "roughening" of the surface of one of the faces of the bag or a thermoformed channel, which aid the flow.

Figure 2:
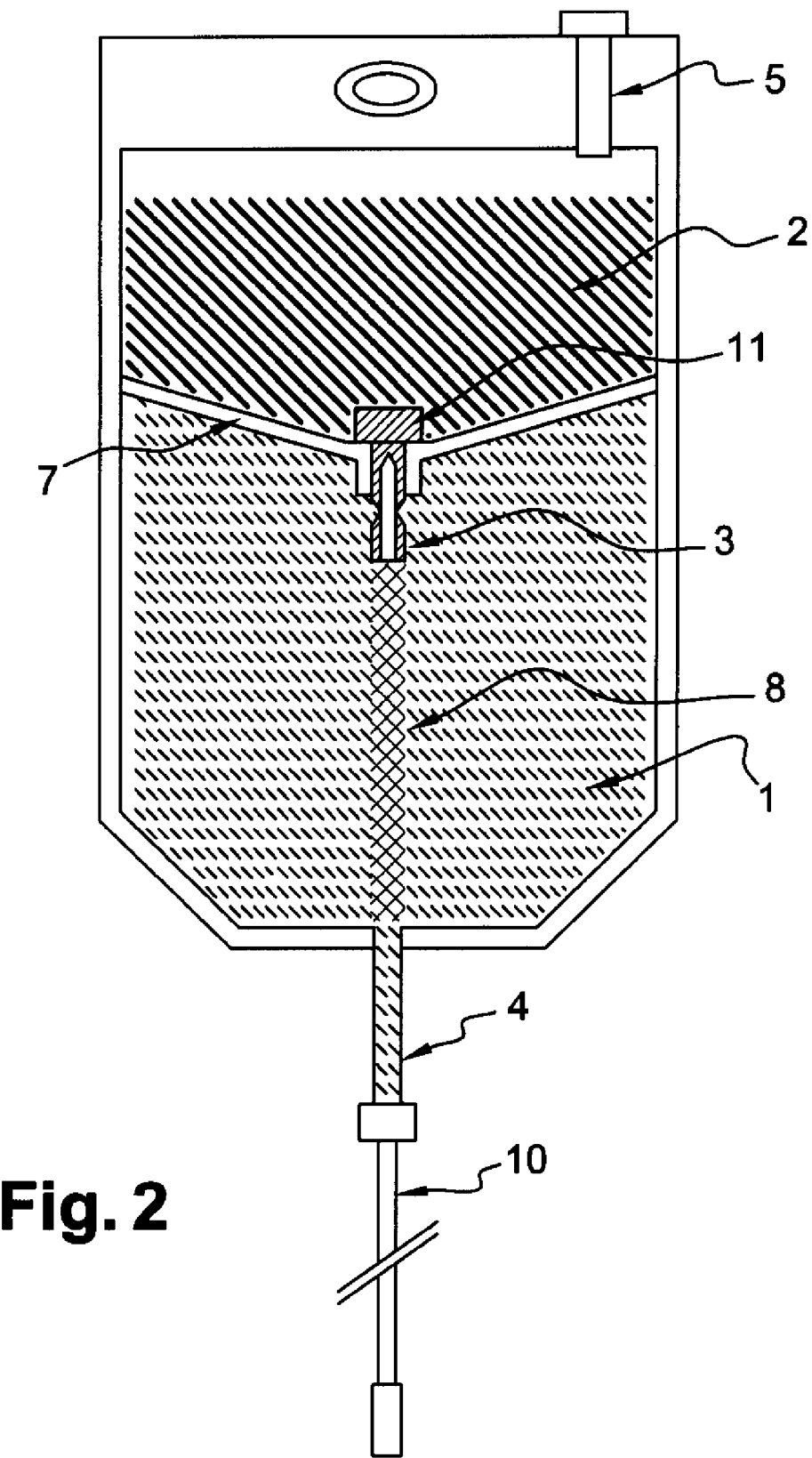
FIG. 2 shows an infusion bag with two compartments comprising a pressure-threshold valve.

According to a second embodiment of the invention shown in FIG. 2, use is made of a flexible infusion bag separated into two superposed compartments (1) and (2). The two compartments are separated by a substantially horizontal wall (7) whose central part comprises a breakable device (3) broken by the nurse. In this embodiment, the flow of the rinsing solution from compartment (2) to compartment (1) is triggered by a pressure-threshold valve (11) as a function of the difference in pressure between the compartments (1) and (2).

Compartment (1) comprises means (8) for preventing the flow path of the liquid from being sealed up completely when the bag flattens. These means (8) facilitate the flow between the communication orifice between the two compartments and the access (4) to the infusion line (10).

According to a variant (not shown) of the bag of FIG. 1 or 2, use is made of two separate bags instead of one bag with two compartments.

Figure 3:
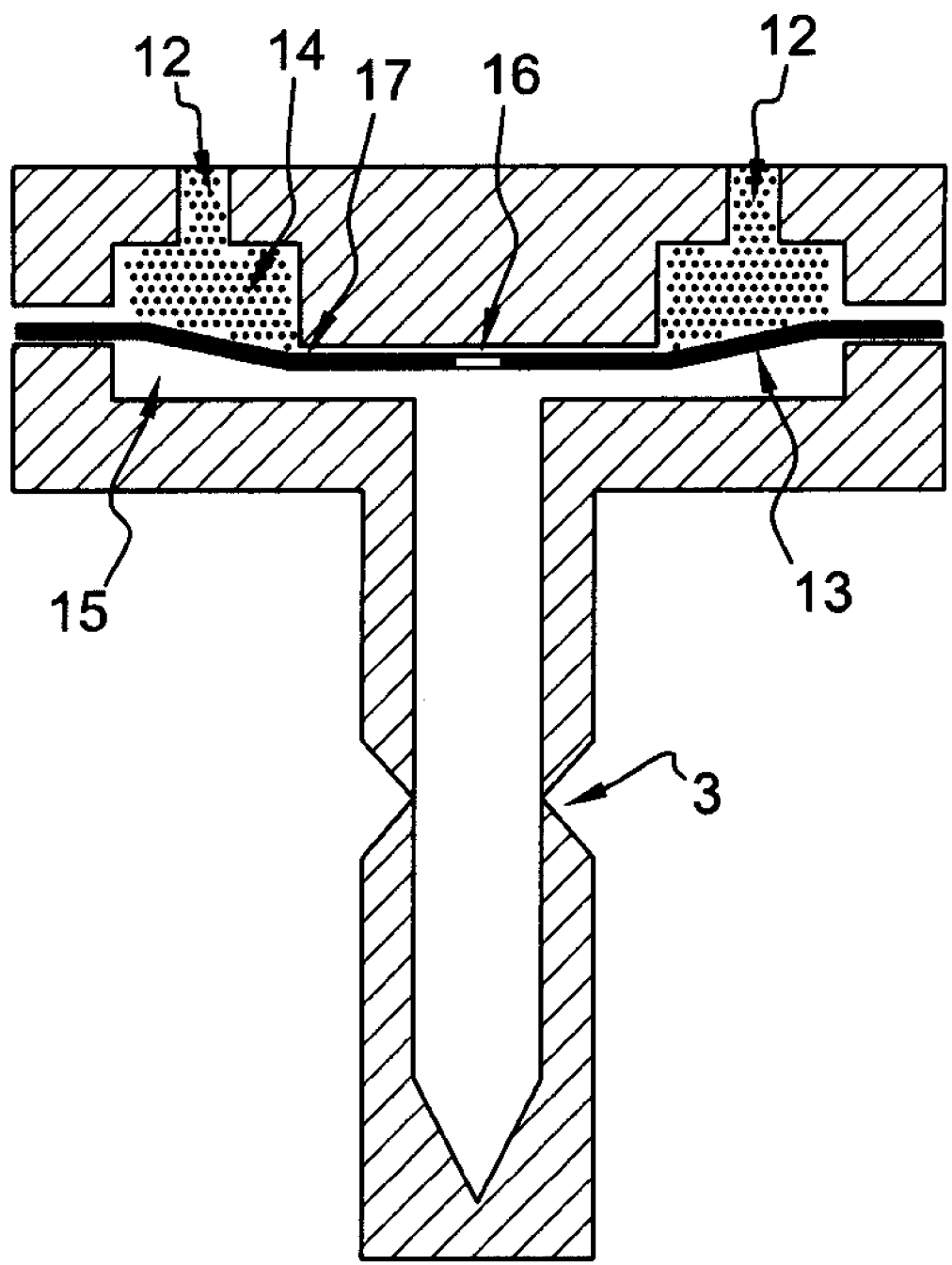
FIG. 3 is a cross section through the pressure-threshold valve of FIG. 2 with integrated breakable device in the closed state.
Figure 4:
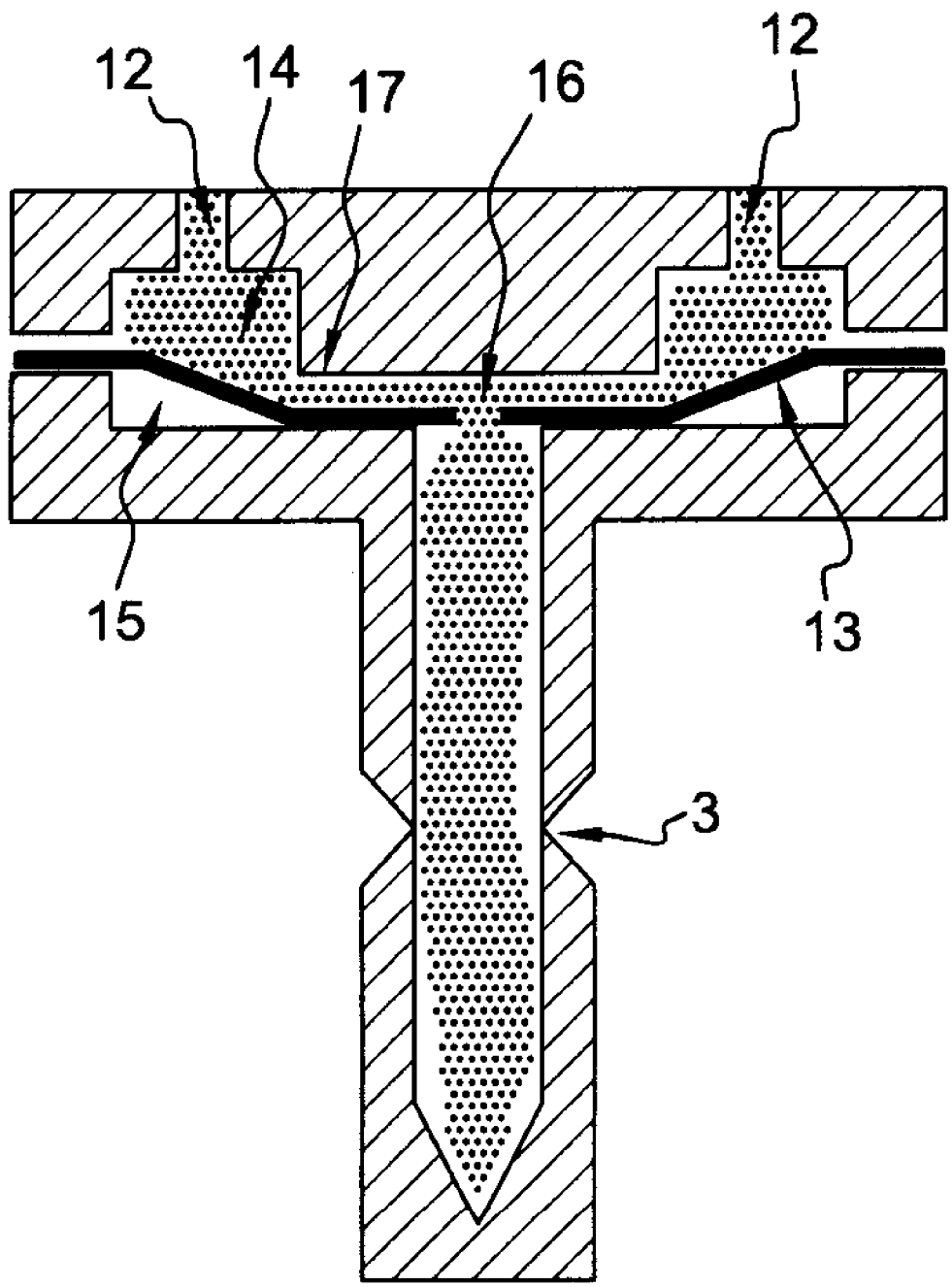
FIG. 4 shows the same valve in the open state.

FIGS. 3 and 4 show an example of the pressure-threshold valve used in the bag of FIG. 2.

The valve comprises two chambers (14) and (15) separated by an elastomer membrane (13). As shown in FIG. 3, the seal between the two chambers is ensured by the membrane (13) being pretensioned on the annular sealing ring (17). The chamber (14) is in communication with compartment (2) containing the rinsing solution via the openings (12). After the breakable device (3) is broken, the chamber (15) is in communication with the compartment (1) containing the medication.

As shown in FIG. 4, when the pressure inside the chamber (15) becomes negative with respect to the pressure in the chamber (14), the membrane (13) detaches from the annular sealing ring (17), thus allowing the rinsing liquid contained in compartment (2) to flow into compartment (1) via the orifice (16).

Figure 5:
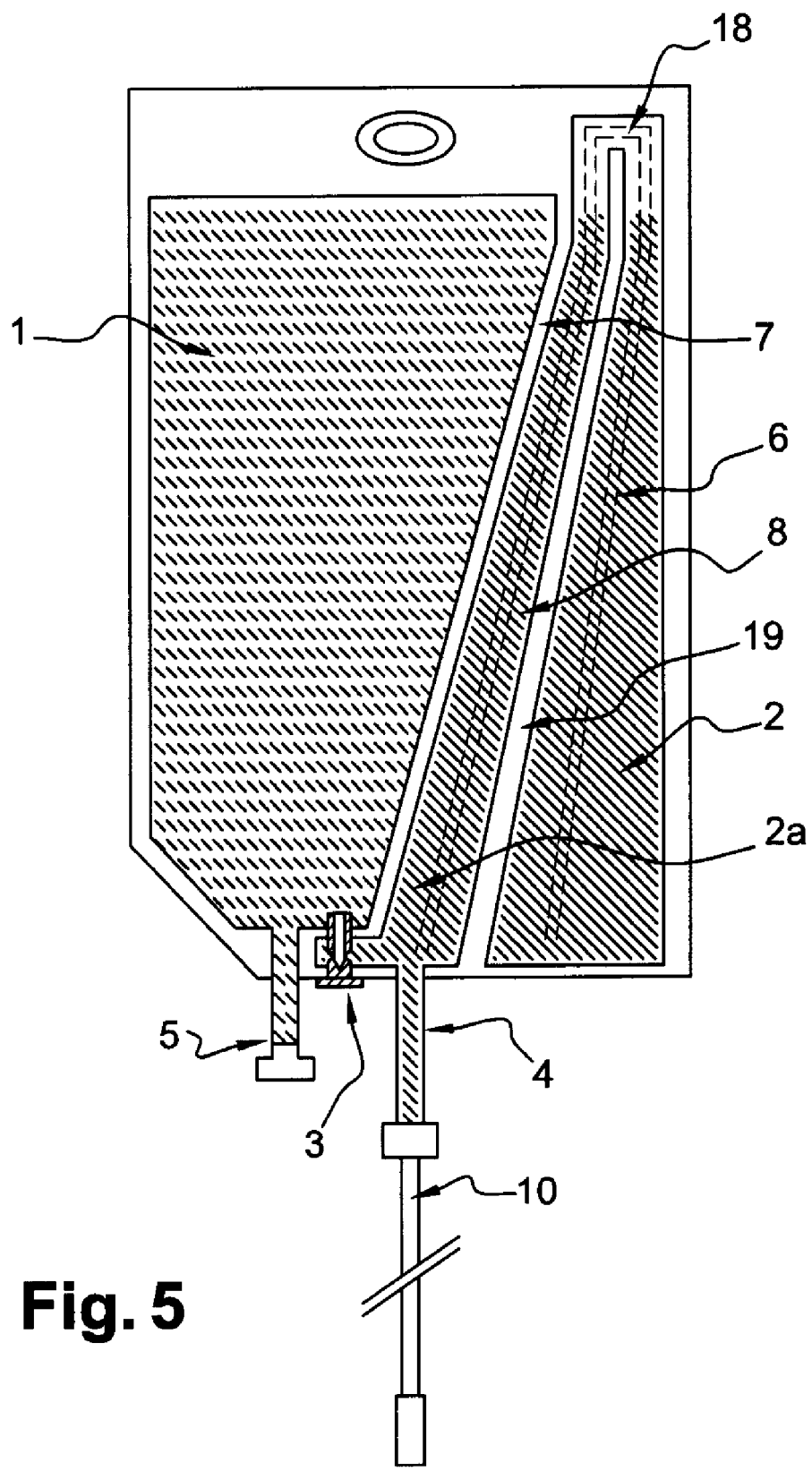
FIG. 5 shows an infusion bag with three compartments comprising a communication channel.

According to a third embodiment of the invention shown in FIG. 5, use is made of a flexible infusion bag separated into three juxtaposed compartments, allowing rinsing at the beginning and end of infusion. Compartment (1) contains the medication and is separated from compartments (2) and (2*a*) containing rinsing solution by a substantially vertical wall (7) whose lower part comprises a breakable device (3) broken by the nurse.

Compartments (2) and (2*a*) are separated by a wall (20) leaving a passage (18) at the top of the bag which prevents the transfer of the contents from (2) into (2*a*) and/or the contents from (2*a*) into (2) if the bag is suspended vertically and if there is no difference in pressure between said compartments. Compartment (2*a*) comprises an access (4) to the infusion line (10). The volume of compartment (2*a*) is slightly greater than the volume of a standard infusion line (around 10 milliliters).

The following examples illustrate how the infusion bags of the invention are used.

Example 1

Bag with Two Juxtaposed Compartments (FIG. 1)

After the infusion line has been established, the nurse breaks the breakable device (3) by mechanical intervention on the outside of the flexible bag, to place the compartments (1) and (2) in communication without causing transfer since the pressure inside the two compartments is identical. When compartment (1) is practically empty, its walls collapse. The pressure in compartment (1) then becomes negative with respect to the pressure in compartment (2), which flattens, causing the rinsing liquid to rise into the communication channel between the two compartments. The rising liquid then empties into compartment (1), and then into the infusion line, thus rinsing the medication out of compartment (1) and the line (10). The patient will thus receive all the medication and the nurse will handle an infusion line and a bag free of toxic liquid.

Example 2

Bag with Two Superposed Compartments (FIG. 2)

The method of example 1 is followed, except that it is the pressure-threshold valve that allows the rinsing solution to flow into compartment (1) when the pressure in this compartment becomes negative with respect to the pressure in compartment (2).

Example 3

Bag with Three Juxtaposed Compartments (FIG. 5)

Once the bag has been connected up to the infusion line (10), the air-filled infusion line is in communication with compartment (2a) which is full of rinsing solution. The nurse starts infusion as usual with the contents of compartment (2a). After this operation, compartment (2a) is almost empty.

The nurse connects the line to the patient, then breaks the breakable device (3). Compartment (1) is then in communication with compartment (2a) and thus with the infusion line (10). The medication contained in (1) flows into compartment (2a) until the heights of liquid in said compartments are equal.

When compartments (1) and (2a) are almost empty, the walls collapse, causing the rinsing solution in compartment (2) to be sucked into compartment (2a). After the levels between compartments (1) and (2a) have equaled out, which rinses the bottom of the compartment, the rinsing solution flows into the perfusion line (10).

The description and figures illustrate various embodiments of the present invention. However, the invention is not limited to the embodiments described and shown but, on the contrary, encompasses all variants.

What is claimed is:

1. A bag for medical use for infusing medication by gravity, comprising:
    at least a first compartment, a second compartment and a third compartment, the first compartment configured to contain medication in the form of a solution, the third compartment configured to contain a first rinsing solution, and the second compartment configured to contain a second rinsing solution, wherein the first compartment, the second compartment and the third compartment are juxtaposed,
    a first separation/communication portion that separates the first compartment and the third compartment,
        wherein the first separation/communication portion comprises a breakable device disposed between the first and the third compartment and the breakable device is disposed at a bottom end of the first separation/communication portion when the bag is suspended vertically, and
    a second separation/communication portion that separates the second compartment and the third compartment,
        wherein the second separation/communication portion comprises a communication channel disposed at an end of the bag that is above the second compartment when the bag is suspended vertically, and
    an access port for an infusion line disposed at a bottom portion of the third compartment when the bag is suspended vertically,
    wherein the breakable device prevents communication between the first compartment and the third compartment when not broken, and the breakable device allows communication between the first compartment and the third compartment when broken,
    wherein if the breakable device is broken, the medication is capable of flowing into the third compartment and flowing into the infusion line via the third compartment, and
    wherein the second rinsing solution is capable of flowing into the third compartment via the communication channel and flowing into the infusion line, after the first compartment and the third compartment are almost emptied,
    wherein the communication channel has an output side disposed at a height that substantially prevents the second rinsing solution from entering the third compartment until after the first compartment and the third compartment are almost emptied of the medication solution, and
    wherein the second separation/communication portion is configured to allow the second rinsing solution to automatically flow into the third compartment via the communication channel when a pressure in the first compartment and the third compartment becomes negative with respect to a pressure in the second compartment under a siphon effect created by a fluid column height in the infusion line.

2. The bag according to claim 1, wherein the second compartment comprises a narrow area at the top of the bag.

3. The bag according to claim 1, further comprising means for preventing the flow path of the second rinsing solution from being sealed completely when the bag flattens.

4. The bag according to claim 3, wherein the means for preventing the flow path of the second rinsing solution from being sealed completely comprises a roughening of the surface of at least one face of the bag.

5. The bag according to claim 3, wherein said means for preventing the flow path of the second rinsing solution from being sealed completely comprises a thermoformed channel.

6. The bag according to claim 1, wherein the bag is flexible.

7. The bag according to claim 1, wherein the first compartment and the third compartment are separated by a substantially vertical wall.

8. The bag according to claim 1, wherein the third compartment and the second compartment are separated by a substantially vertical wall.

* * * * *